July 12, 1938. F. M. BOWERS Re. 20,790

HEADGEAR FRICTION JOINT DEVICE FOR WELDING SHIELDS

Original Filed Oct. 1, 1937 2 Sheets-Sheet 1

INVENTOR.
FREDERICK M. BOWERS.
BY Joshua R. H. Potts
ATTORNEY.

July 12, 1938. F. M. BOWERS Re. 20,790

HEADGEAR FRICTION JOINT DEVICE FOR WELDING SHIELDS

Original Filed Oct. 1, 1937 2 Sheets-Sheet 2

INVENTOR.
FREDERICK M. BOWERS.
BY Joshua R. H. Hopkins
ATTORNEY.

Reissued July 12, 1938

Re. 20,790

UNITED STATES PATENT OFFICE 20,790

HEADGEAR FRICTION JOINT DEVICE FOR WELDING SHIELDS

Frederick M. Bowers, Chester, Pa.

Original No. 2,111,747, dated March 22, 1938, Serial No. 166,797, October 1, 1937. Application for reissue April 16, 1938, Serial No. 202,473

7 Claims. (Cl. 2—8)

Figure 1:
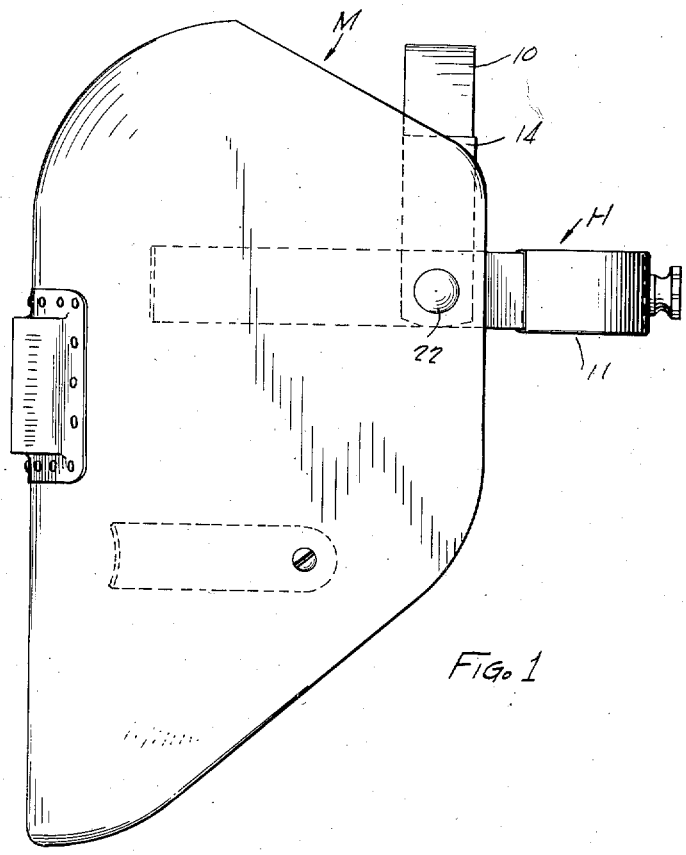

This invention relates to welding shields and similar protective devices, and is concerned primarily with that type of a shield in which the shield or mask that protects the front of a person's head is pivotally mounted on a headband.

When a shield of the character above noted is worn, the headband is snugly and more or less positively positioned on the head of the wearer. The mask or shield which covers the wearer's face is pivotally mounted on this headband, as it must be swung into and out of effective shielding position many times during the course of welding operations.

The present invention has in view, as its foremost objective, the provision of a friction device which is designed to be located at the pivotal mounting of the shield for creating frictional resistance to swinging movement of the mask whereby the mask will remain in any adjusted position.

It is now a known practice in this art to employ a headband that includes as an essential part thereof a cross strip that fits over the top of the head of the wearer. This strip is anchored at each end to the band that goes around the head of the wearer. Heretofore it has been the practice to turn back the extremity of the cross piece beyond the connection of the latter to the headband, and anchor the free extremity to the cross piece, thus providing a loop formation at each side of the headband, and the mask itself has been pivotally mounted to the outer side pieces of these loops.

In accordance with the present invention the loop construction is eliminated and replaced by bracket strips that are anchored at one end to the cross piece of the headband, and which are pivotally connected at their free ends to the mask. Interposed between the free ends of these bracket strips and the headband are the frictional devices of the present invention.

The invention has in view, as a further more detailed objective, the provision of a friction device of the character above noted which may be readily adjusted to vary the friction afforded thereby. In carrying out this idea in a practical embodiment it is important that the friction device itself retain any condition into which it may be adjusted, and a further more detailed object of the invention is to provide a device which will satisfy this condition.

A further object is the provision of a friction device of the character above noted which is readily adjustable from the exterior of the welding shield on which the friction device is assembled.

During service usage of welding shields of the type with which this invention is concerned the shield is swung back and forth on its pivotal mountings on the headband many times, and due to the fact that the friction devices are associated with the pivotal mountings it becomes important to provide a friction device which may be adjusted to vary the frictional resistance offered thereby, and which adjustment is in no way affected by pivotal movement of the shield.

Various other more detailed objects and advantages of the invention, such as those associated with the carrying out of the above noted objectives, will in part become apparent and in part be hereinafter stated, as the description of the invention proceeds.

The invention, therefore, comprises a friction device that is adapted to be located at the pivotal mounting of a welding shield mask on a headband. This friction device is effective to establish frictional resistance to swinging movement of the shield with respect to the headband whereby the shield may be swung into any desired position and be retained in that position by the friction device. The friction device of this invention includes as characteristic features the ability to be adjusted to vary the frictional resistance afforded thereby, and to retain any adjusted position. The friction device may be adjustable from the exterior of the shield on which it is mounted, and adjustment of the device is entirely independent of pivotal movement of the shield.

Figure 2:
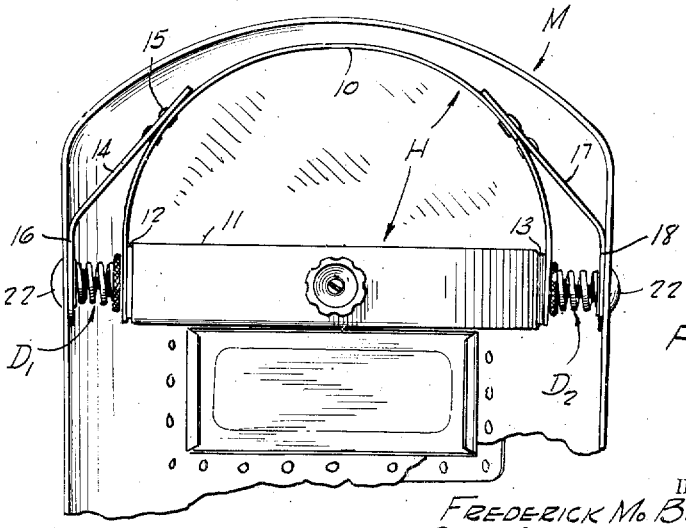
Figure 3:
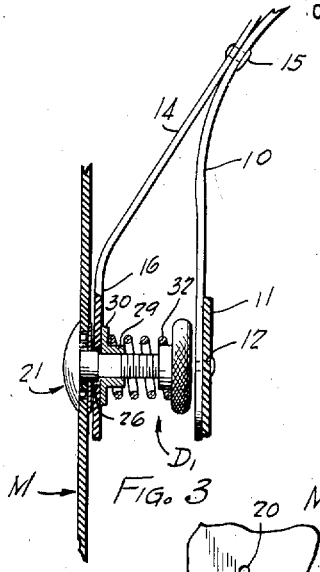
Figure 4:
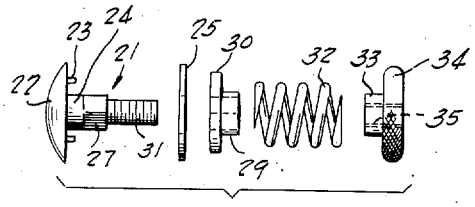
Figure 5:
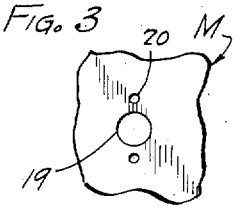
Figure 9:
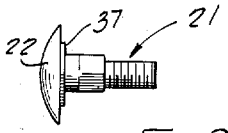
Figure 6:
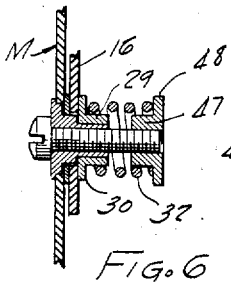
Figure 7:
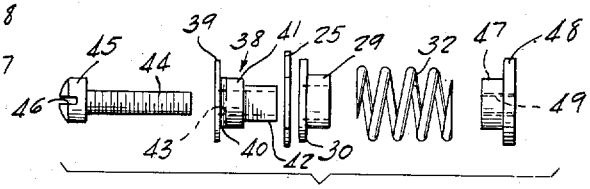
Figure 8:
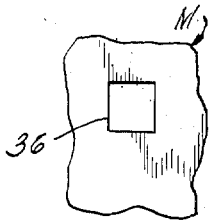
Figure 10:
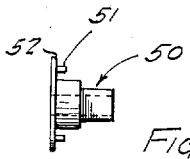

For a full and more complete understanding of the invention reference may be had to the following description and accompanying drawings, wherein Figure 1 is a view in side elevation of a welding shield which includes friction devices of the present invention, Figure 2 is a view taken at right-angles to the showing of Figure 1, looking at the shield from the back, Figure 3 is an enlarged detailed showing taken as a vertical section through the pivotal mounting for the shield at one side, Figure 4 is an elevational showing of the several elements making up the friction device in an exploded relationship, Figure 5 is a detailed showing of part of the welding shield immediately about the pivotal mounting therefor, Figure 6 is a sectional showing somewhat similar to Figure 3 of a modification, Figure 7 is a view in side elevation developing the several elements of the modification of Figure 6 in an exploded relationship, Figure 8 is a view developing the formation of the opening in the shield, Figure 9 is a view developing a further modification which may be carried out, and Figure 10 is a view of still another modification.

Referring now to the drawings, wherein like reference characters denote corresponding parts, a welding helmet of the type with which this invention is primarily concerned is shown in Figures 1 and 2 as comprising a shield or mask element referred to in its entirety by the reference character M, and a headband which is referred to in its entirety by the reference character H.

The headband H includes as an essential part thereof a cross piece 10 that is intended to fit over the top of the head of a wearer. This cross piece 10 is anchored to the strip 11 which fits about the wearer's head at each end, as represented at 12 and 13. Above the connection 12 a bracket strip 14 is anchored to the cross piece 10, as by the rivets illustrated at 15. The bracket strip 14 has a foot portion 16 that is spaced from the connection at 12, and is in engagement with the inner face of the mask M. It is this foot portion 16 of the bracket 14 which constitutes the pivotal mounting for the mask M at that side of the shield.

A friction device which is referred to in its entirety by the reference character $D_1$ is interposed between the connection 12 and foot portion 16 of the bracket strip 14, and this friction device $D_1$ includes as certain essential parts thereof the pivotal mounting for the mask M, as will be later pointed out.

The structure described in the preceding paragraph is duplicated at the opposite side of the shield, which includes the bracket strip 17 having a foot portion 18, with a second friction device $D_2$ interposed between the connection 13 and foot portion 18.

Inasmuch as the friction devices $D_1$ and $D_2$ will be of identical construction in any complete assembly, only one of these devices need be here described for the purpose of this specification. Accordingly reference is made to Figures 3, 4, and 5 for a more complete and detailed description of one of these devices.

The mask M is shown as formed with a circular opening 19, and on each side of the opening 19 are a pair of small recesses 20, for a purpose to be hereinafter described.

A bearing pin referred to in its entirety as 21 is formed with a head 22 the under face of which is adapted to engage the outer surface of the mask M about the hole 19. This under face of the head 22 is provided with a pair of pins 23 that are received in the recesses 20. It is evident that this arrangement prevents relative rotation between the pin 21 and mask M.

Immediately adjacent to the head 22 the pin 21 is formed with a cylindrical portion 24 that extends through the opening 19. A washer 25 is disposed about the cylindrical portion 24 of the bearing pin 21, and is interposed between the mask M and the foot portion 16 of the bracket strip 14. This foot portion 16 is formed with an opening 26 through which the pin 21 passes.

Immediately adjacent the cylindrical portion 24 the pin 21 is formed with a non-circular section such as the square shaped part shown at 27. This square shaped portion 27 of the pin 21 is received in a complementally shaped recess that is formed in a flanged bushing 29; this bushing 29 having a flange 30 that engages the foot portion 16 about the opening 26.

From the square shaped portion 27 the bearing pin 21 is reduced in diameter and threaded for the remainder of its extent, as shown at 31. A coil spring designated 32 is disposed about the bearing pin 31, and has one end seated on the bushing 29 and in engagement with the flange 30. At the opposite end the spring 32 fits about a bushing 33 and engages a flange 34 that is knurled to facilitate its being gripped for rotative purposes. This bushing 33 is provided with a threaded bore represented at 35 which receives the correspondingly threaded portion 31 of the bearing pin 21.

The bottom face of the flange portion 34 of the bushing 33 is spaced from the extremity of the cross piece 10 at the connection 12.

When the foregoing parts are assembled with the bushing 33 threaded on the bearing pin 21, the spring 32 will be under compression, and will exert a tendency to spread the bushing 29 away from the bushing 33. Thus the flange portion 30 of the bushing 29 is pressed against the foot portion 16 which engages the washer 25 on the other side, and a frictional resistance to rotative movement of the foot portion 16 is set up, and the degree of this frictional resistance is directly dependent upon the tension under which the coil spring 32 is placed. Thus by tightening the bushing 33 to further compress the spring 32 greater tension is placed on the spring, and in a converse manner the tension of this spring may be reduced.

An important feature of the above described mechanical assembly is the non-rotative relationship established from the mask M through the bushing 29. It is evident that the bearing pin 21 is held in a non-rotative relationship with respect to the mask M by the pins 23 fitting in the recesses 20, and the bushing 29 in turn is non-rotatably mounted on the pin 21 by the squared formation 27 and the correspondingly shaped opening in the bushing 29. Thus the spring 32 cannot possibly affect the bushing 29 to cause any turning thereof.

This non-rotative relationship between the bearing pin 21 and the mask M may be obtained in a slightly modified manner, as is shown by reference to Figures 8 and 9. In such a case the mask M is shown as formed with a square shaped opening 36, and the pins 23 of the bearing pin 21 are replaced by a squared formation shown at 37 that is complemental to the squared opening 36. Thus when the square part 37 on the under side of the head 22 is received in the opening 36, rotation between these parts is prohibited.

In the embodiment of the invention above described it is evident that the adjustment in the frictional resistance afforded by the device is obtained by rotating the knurled flange 34 which is disposed within the shield. In the modification of the invention shown in Figures 6 and 7 the adjustment is obtained from the exterior of the shield. In this form of the invention a bearing member 38 is shown as having a head 39 that engages the outer wall of the mask M, and immediately adjacent the under side of the head 39 is a squared portion 40 which is complemental to the squared opening 36; the squared portion 40 being received in the squared opening 36, and is thus non-rotatably positioned with respect to the mask M.

Adjacent the squared portion 40 the bearing member 38 is formed with a cylindrical portion 41 that extends through an opening in the washer 25 and also into the opening 26 in the foot portion 16. The bearing member 38 also includes a squared portion 42 that extends into the complementally shaped opening in the bushing 29.

The bearing member 38 is formed with a bore designated 43, and extending into the bore 43 is a threaded pin 44 having a head 45 that is provided with a slot 46 which constitutes means for rotating the pin 44. The assembly of the device shown in Figures 6 and 7 also includes the spring 32 and a bushing 47 that corresponds to the bushing 33 in the previously described mechanism. This bushing 47 is flanged, as shown at 48, and is provided with a threaded bore at 49 for receiving the threaded pin 44.

The various parts of the assembly of Figures 6 and 7 are assembled in the same manner as above described in connection with the mechanism of Figures 3 and 4, with the spring 32 being contained between the bushings 29 and 47. The tension offered by the spring to establish a frictional resistance depends on the distance between these bushings, and this distance may be varied by rotating the stem 44 through the medium of the slot 46 in the head 45.

The above described mechanism of Figures 6 and 7 avails of the squared opening 36 as the means for establishing the non-rotative relationship between the bearing member 38 and the mask M. However, this arrangement may be replaced by availing of the small recesses 20 at each side of the main opening, as shown in Figure 5, and employing a bearing member, shown at 50 in Figure 10, which includes pins 51 on the under face of the head 52. In all other repects this bearing member 50 is similar to the bearing member 38 shown in Figures 6 and 7.

The establishment of the non-rotative relationship between the bearing member 38 and the mask M for the form of the invention shown in Figures 6 and 7, and between the bearing pin 21 and mask M for the form of the invention shown in Figures 3 and 4, is of importance because it provides for the friction device maintaining any degree of tension to which it might be adjusted irrespective of any swinging movement of the mask M on its pivotal mounting. Thus the mask M may be swung back and forth as required during service usage, without in any way affecting the degree of frictional resistance which is offered by the friction devices.

While preferred specific embodiments of the invention are hereinbefore set forth it is to be clearly understood that I am not to be limited to the exact constructions illustrated and described, because various modifications of these details may be provided in putting the invention into practice within the purview of the appended claims.

I claim:

1. A protective device of the character described comprising a headband adapted to be mounted on the head of a wearer, said headband consisting of a strip adapted to fit around the head of a wearer, and a cross piece connected at each end to the said strip and adapted to extend over the top of the head of a wearer, a bracket strip anchored at one end to the cross piece and having its free end in spaced relation to the headband, a shield pivotally mounted on the free end of said bracket strip, and a friction device interposed between the free end of said bracket strip and the headband.

2. A protective device of the character described comprising a headband adapted to be mounted on the head of a wearer, said headband consisting of a strip adapted to fit around the head of a wearer, and a cross piece connected at each end to the said strip and adapted to extend over the top of the head of a wearer, a bracket strip anchored at one end to the cross piece and having its free end in spaced relation to the headband, a shield and bearing member for pivotally mounting the shield on the free end of said bracket strip, and a device for establishing frictional resistance disposed about said bearing pin and interposed between the free end of said bracket strip and the headband.

3. In a protective device of the character described including a headband and a shield pivotally mounted on the headband, a device for establishing frictional resistance to pivotal movement of the shield with respect to the headband comprising a bearing pin extending through an opening in the shield and in non-rotative relationship with respect thereto, said bearing pin also extending through an opening in a part of the headband, a bushing non-rotatably carried by said bearing pin, a second bushing threaded on the end of said bearing pin, and a spring interposed between said bushings, said spring exerting a tendency urging the first mentioned bushing into engagement with the said part of the headband.

4. In a protective device of the character described including a shield and a headband having bracket strips the free ends of which are spaced from the headband and pivotally connected to the shield, a friction device comprising a bearing pin extending through an opening in the mask, means for establishing non-rotative relationship between the bearing pin and the mask, said bearing pin also extending through an opening in the bracket strip, a washer interposed between the bracket strip and the mask, a flanged bushing non-rotatably carried by the bearing pin and engaging the bracket strip, a second flanged bushing threaded on the end of said bearing pin, and a coil spring interposed between said flanged bushings.

5. In a protective device of the character described including a shield and a headband having bracket strips the free ends of which are spaced from the headband and pivotally connected to the shield, a friction device comprising a bearing member having a bore, said bearing member extending through an opening in the shield, means for establishing a non-rotative relationship between the bearing member and the shield, said bearing member also extending through an opening in the bracket strip, a flanged bushing non-rotatably carried by said bearing member, a threaded pin extending through the bore of said bearing member and therebeyond, a second flanged bushing threaded on said pin and in spaced relation to said first mentioned flanged bushing, and a coil spring interposed between said flanged bushings, and means on said pin for rotating the same.

6. A protective device of the character described comprising a headband adapted to be mounted on the head of a wearer, said headband consisting of a strip adapted to fit around the head of a wearer, and a cross piece connected at each end to the said strip and adapted to extend over the top of the head of a wearer, said cross piece carrying at each end a bracket strip, a shield pivotally mounted in said bracket strips, and friction devices interposed between the bracket strips and the headband and associated with the pivotal mountings of the shield, each of said friction devices including a spring the tension of which determines the frictional resistance offered by the device, and means operable from the exterior of the shield for adjusting the tension of said spring.

7. In a protective device of the character described including a shield pivotally mounted on the headband, a friction device comprising a bearing member having a bore, said bearing member extending through an opening in the shield, means for establishing a non-rotative relationship between the bearing member and the shield, a bushing non-rotatably carried by said bearing member, a threaded pin extending through the bore of said bearing member and through the bushing, a second bushing threaded on said pin and in spaced relation to said first mentioned bushing, a coil spring interposed between said bushings, and means on said pin for rotating the same.

FREDERICK M. BOWERS.